(12) United States Patent
Duran et al.

(10) Patent No.: US 8,207,335 B2
(45) Date of Patent: Jun. 26, 2012

(54) PROCESS FOR MAKING CERTAIN COMPOUNDS HAVING B1 ANTAGONISTIC ACTIVITY

(75) Inventors: Adil Duran, Biberach (DE); Markus Frank, Ingelheim am Rhein (DE); Waldemar Pfrengle, Biberach (DE); Juergen Schnaubelt, Oberhoefen/Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 234 days.

(21) Appl. No.: 12/702,097

(22) Filed: Feb. 8, 2010

(65) Prior Publication Data

US 2010/0210842 A1 Aug. 19, 2010

(30) Foreign Application Priority Data

Feb. 13, 2009 (EP) .................................. 09152777

(51) Int. Cl.
*C07D 295/155* (2006.01)
(52) U.S. Cl. .................. 544/400; 514/255.03
(58) Field of Classification Search .................. 544/400; 564/89
See application file for complete search history.

(56) References Cited

U.S. PATENT DOCUMENTS

| 4,220,761 A | * | 9/1980 | Takaya et al. ................. 540/227 |
| 2006/0178360 A1 | * | 8/2006 | Barth et al. ............... 514/217.03 |
| 2011/0098282 A1 | * | 4/2011 | Hauel et al. .................... 514/218 |

FOREIGN PATENT DOCUMENTS

WO 2009/021944 * 2/2009

* cited by examiner

*Primary Examiner* — Emily Bernhardt
(74) *Attorney, Agent, or Firm* — Michael P. Morris; Alan R. Stempel

(57) ABSTRACT

The present invention relates to a method of preparing compounds of general formula I

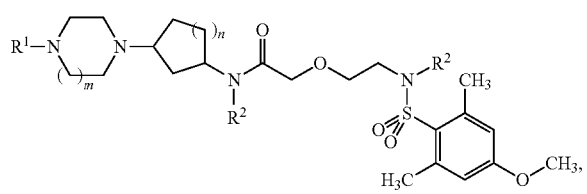

(I)

wherein m, n, $R^1$ and $R^2$ are defined as mentioned hereinafter, the enantiomers, the diastereomers, the mixtures and the salts thereof, particularly the physiologically acceptable salts thereof with organic or inorganic acids or bases.

2 Claims, No Drawings

PROCESS FOR MAKING CERTAIN COMPOUNDS HAVING B1 ANTAGONISTIC ACTIVITY

The present invention relates to a method of preparing compounds of general formula I

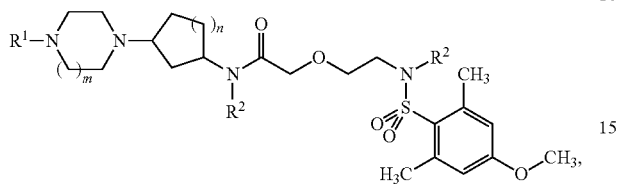

wherein m, n, $R^1$ and $R^2$ are defined as mentioned hereinafter, the enantiomers, the diastereomers, the mixtures and the salts thereof, particularly the physiologically acceptable salts thereof with organic or inorganic acids or bases.

BACKGROUND TO THE INVENTION

Technical Field

The present invention relates to an industrial method of preparing compounds of general formula I which have B1-antagonistic properties. In addition, the invention relates to the compounds of general formulae V per se, as they are particularly suitable for preparing the compounds of general formula I.

DETAILED DESCRIPTION OF THE INVENTION

In a first aspect the present invention relates to a method of preparing compounds of general formula I

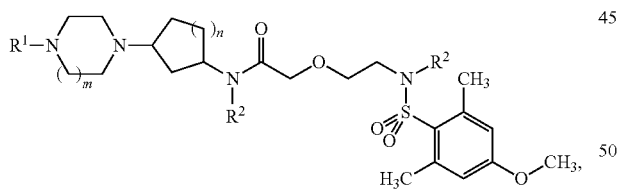

wherein
m denotes the number 1 or 2,
n denotes the number 0, 1 or 2,
$R^1$ denotes $C_{1-3}$-alkyl or $C_{3-6}$-cycloalkyl and
$R^2$ denotes H or $C_{1-3}$-alkyl,
the enantiomers, the diastereomers, the mixtures and the salts thereof, particularly the physiologically acceptable salts thereof with organic or inorganic acids or bases, comprising the steps of:
(a) reacting 3,5-dimethylanisol with chlorosulphonic acid;
(b) reacting 4-methoxy-2,6-dimethylsulphonyl chloride obtained in step (a) with a compound of general formula II

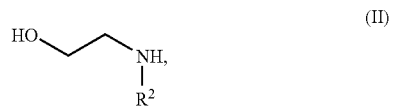

wherein $R^2$ is defined as mentioned hereinbefore;
(c) reacting a compound of general formula III obtained in step (b)

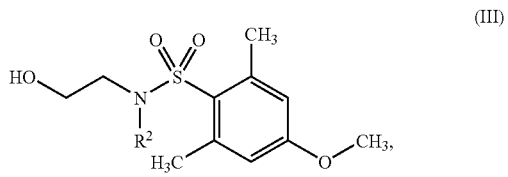

wherein $R^2$ is defined as mentioned hereinbefore, with a compound of general formula IV

wherein X denotes a hydrogen atom, an alkali metal, for example lithium, sodium or potassium, or a $C_{1-4}$-alkyl group, but preferably sodium, and Y denotes a halogen atom, for example chlorine or bromine, preferably chlorine;
(d) optionally recrystallising a compound of general formula V obtained in step (c)

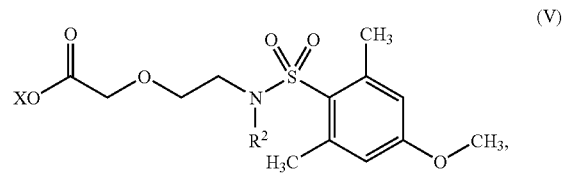

wherein $R^2$ is defined as mentioned hereinbefore and X denotes a hydrogen atom, an alkali metal, for example lithium, sodium or potassium, or a $C_{1-4}$-alkyl group, but preferably sodium, from a solvent;
(e) coupling a compound of general formula V obtained in step (c) or (d)

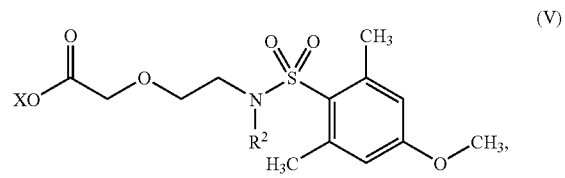

wherein $R^2$ is defined as mentioned hereinbefore and X denotes a hydrogen atom, an alkali metal, for example lithium, sodium or potassium, or a $C_{1-4}$-alkyl group, but preferably sodium, with a compound of general formula VI $$R^1-N\underset{(\phantom{N})_m}{\overset{\phantom{N}}{\bigcirc}}N-\underset{\underset{R^2}{|}}{\overset{(\phantom{N})_n}{\bigcirc}}NH \quad X \quad \text{o HCl}, \qquad \text{(VI)}$$

wherein m, n, R$^1$ and R$^2$ are defined as mentioned hereinbefore and o denotes one of the numbers 0, 1, 2 or 3, preferably 3; and (f) isolating a compound of general formula I obtained in step (d).

In the reaction under step (a) preferably 1.0 equivalents of 3,5-dimethylanisol are reacted with 1.5 to 2.5 equivalents, preferably 1.8 to 2.2 equivalents, of chlorosulphonic acid. The reaction may be carried out in a solvent which is selected from among dichloromethane, chloroform and 1,2-dichloroethane. The solvent may be used in an amount of from 0.25 to 1.25 L/mol, preferably 0.60 to 0.90 L/mol of the 3,5-dimethylanisol used.

Preferably the reaction is carried out at low temperature, for example between −40° C. and 0° C., preferably between −30° C. and 0° C., more preferably between −35° C. and −10° C., more preferably between −20° C. and −10° C.

In the reaction under step (b) preferably 1.0 equivalents 2,6-dimethyl-4-methoxy-sulphonyl chloride are reacted with 1.5 to 2.5 equivalents, preferably 1.8 to 2.2 equivalents, of a compound of general formula II.

The reaction may be carried out in a solvent which is selected from among dichloromethane, chloroform and 1,2-dichloroethane. The solvent may be used in an amount of 0.25 to 1.25 L/mol, preferably 0.5 to 1.0 L/mol of the 2,6-dimethyl-4-methoxy-sulphonyl chloride used.

Preferably the reaction is carried out at a temperature which is below ambient temperature, for example between −0° C. and 20° C., preferably between 5° C. and 15° C.

In the reaction under step (c), preferably 1.0 equivalents of a compound of general formula III are reacted with 1.1 to 2.5 equivalents, preferably 1.4 to 1.7 equivalents, of a compound of general formula IV.

The reaction may be carried out in a solvent which is selected from among acetonitrile, tetrahydrofuran, methyltetrahydrofuran, acetone, toluene, xylene, dichloromethane and chloroform. The solvent may be used in an amount of 0.5 to 3 L/mol, preferably 1.2 to 1.7 L/mol of the compound of general formula III used.

Moreover, a base may be added to the reaction mixture. The base may be selected from among potassium tert. butoxide, potassium carbonate, sodium carbonate, lithium carbonate, sodium hydride, sodium methoxide and sodium ethoxide, preferably potassium tert. butoxide. It may be added in an amount of 1.2 to 2.0 equivalents, preferably 1.3 to 1.6 equivalents, based on the amount of compound of general formula III used.

The compound of general formula V obtained in step (c) may be purified before the reaction described in step (e) by recrystallisation from a solvent which is selected from among water, tetrahydrofuran, methyltetrahydrofuran, acetone or the mixtures thereof.

In the coupling under step (e) preferably 1.0 equivalents of a compound of general formula VI are reacted with 1.0 to 1.5 equivalents, preferably 1.0 to 1.2 equivalents, of a compound of general formula V.

The reaction may be carried out in a solvent which is selected from among tetrahydrofuran, methyltetrahydrofuran, dichloromethane, toluene, ethyl acetate, isopropyl acetate and dioxane. The solvent may be used in an amount of 1.2 to 2 L/mol, preferably 1.4 to 1.8 L/mol of the compound of general formula VI used.

Moreover, a base may be added to the reaction mixture. The base may be selected from among potassium tert. butoxide, sodium hydroxide, potassium hydroxide, potassium carbonate, sodium carbonate, triethylamine, diisopropylethylamine and diazabicyclo[5.4.0]undec-7-ene (DBU), preferably potassium tert. butoxide. It may be added in an amount of 3 to 4 equivalents, preferably 3.3 to 3.8 equivalents, based on the amount of compound of general formula VI used.

In addition, a coupling reagent may be added to the reaction mixture. The coupling reagent may be selected from among propanephosphonic anhydride, thionyl chloride, N,N,N',N'-tetramethyl-O-(benzotriazol-1-yl)uronium tetrafluoroborate, carbodiimide and 1,1'-carbonyldiimidazole; according to the invention propanephosphonic anhydride is preferably used.

Preferably the reaction is carried out at elevated temperature, for example between 40° C. and 60° C.

The isolation described under (f) is preferably carried out by evaporation to dryness or crystallisation from water or dichloromethane, methanol, ethanol, propanol, butanol, isopropyl acetate, ethyl acetate, tetrahydrofuran, methyltetrahydrofuran, dioxane, methylisobutylketone, toluene, xylene or mixtures of these solvents, while water, ethanol, tetrahydrofuran, ethyl acetate, methylisobutylketone and toluene or mixtures thereof are preferably used.

In a second aspect the present invention relates to a method described hereinbefore in the first aspect for preparing compounds of general formula I, characterised in that m denotes the number 1, n denotes the number 1, R$^1$ denotes C$_{1-3}$-alkyl and R$^2$ denotes H or C$_{1-3}$-alkyl, the enantiomers, the diastereomers, the mixtures and the salts thereof, particularly the physiologically acceptable salts thereof with organic or inorganic acids or bases.

In a third aspect the present invention relates to the compounds of general formla V $$\text{XO}\underset{}{\overset{O}{\diagdown}}\diagdown O\diagdown\diagdown N\underset{R^2}{|}\overset{O\diagdown\diagup O}{S}\diagdown\underset{H_3C}{\overset{CH_3}{\bigcirc}}\diagdown O\diagdown CH_3, \qquad (V)$$

wherein

R$^2$ denotes H or C$_{1-3}$-alkyl and

X denotes hydrogen, lithium, sodium, potassium or a C$_{1-4}$-alkyl group, preferably sodium.

A preferred third aspect encompasses the following compounds Va to Vd of general formula V:

| No. | Structure | |
|---|---|---|
| (1) | 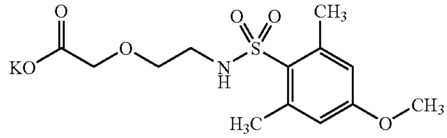 | Va |
| (2) | 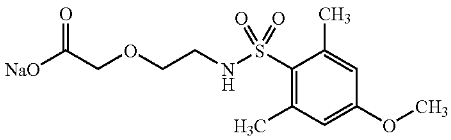 | Vb |
| (3) | 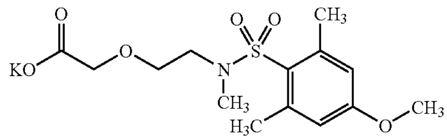 | Vc |
| (4) | 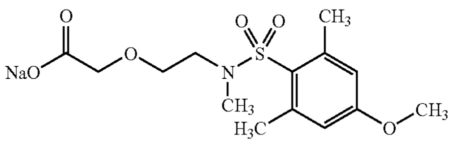 | Vd |
| (5) | 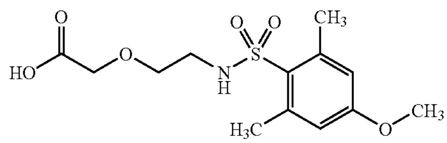 | Ve |
| (6) | 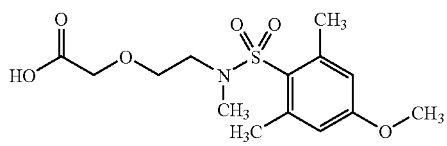 | Vf |

A more preferred third aspect relates to the compound of formula Vd

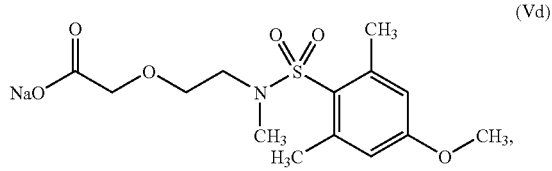
(Vd)

which occurs in crystalline form and is characterised by a high degree of stability.

The crystalline compound of formula Vd is characterised by a characteristic melting point of T=152±3° C. The stated value was determined by differential using a melting point measuring apparatus (Mettler Toledo FP90 Central, 5° C./min in the range from 50-150° C. and/or 1° C./min in the range from 100-180° C.).

In a fourth aspect the present invention relates to the use of the above-mentioned compounds of general formula V as intermediate products for preparing compounds of general formula I according to a method described hereinbefore in the first embodiment.

TERMS AND DEFINITIONS USED

The subject-matter of this invention also encompasses the compounds according to the invention, including their salts, wherein one or more hydrogen atoms, for example one, two, three, four or five hydrogen atoms, are replaced by deuterium. Also included in the subject-matter of this invention are the compounds according to the invention, including their salts, wherein one or more $^{13}C$ carbon atoms are replaced by $^{14}C$.

By the term "$C_{1-3}$-alkyl" (including those that are part of other groups) are meant branched and unbranched alkyl groups with 1 to 3 carbon atoms and by the term "$C_{1-4}$-alkyl" are meant branched and unbranched alkyl groups with 1 to 4 carbon atoms. Examples include: methyl, ethyl, n-propyl, iso-propyl, n-butyl, iso-butyl or tert.-butyl. The abbreviations Me, Et, n-Pr, i-Pr, n-Bu, i-Bu, tert-Bu etc. are optionally also used for the above-mentioned groups.

By the term "$C_{3-6}$-cycloalkyl" (including those that are part of other groups) are meant cycloalkyl groups with 3 to 6 carbon atoms. Examples include: cyclopropyl, cyclobutyl, cyclopentyl or cyclohexyl.

The compounds of general formula I may have basic groups such as e.g. amino functions. They may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid or citric acid.

Preferably the compounds of general formula I may be present as salts or co-crystals with chiral organic acids. Examples of suitable chiral acids include in particular chiral amino acids, tartaric acid, tartaric acid derivatives, chiral sulphonic acids such as for example (S)-(+)-camphorsulphonic acid, camphanic acid, camphanic acid derivatives, mandelic acid or malic acid, of which (S)-(+)-camphorsulphonic acid is of exceptional importance.

The invention relates to the respective compounds optionally in the form of their individual optical isomers, enantiomers or diastereomers, mixtures of the individual enantiomers or racemates, in the form of their tautomers and in the form of the free bases or the corresponding acid addition salts.

EXPERIMENTAL SECTION

Example 1

N-(2-hydroxy-ethyl)-4-methoxy-2,6,N-trimethyl-benzenesulphonamide (C)

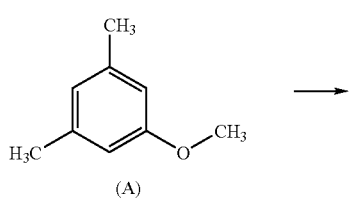
(A)

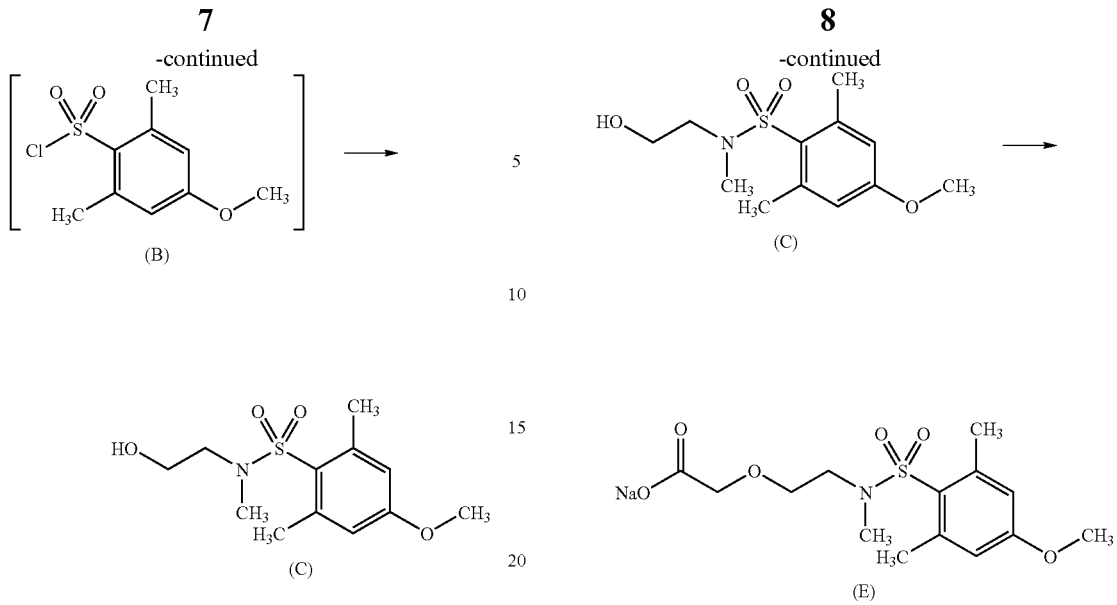

10.00 kg (73.42 mol) of 3,5-dimethylanisol (A) were dissolved in 35.0 L of dichloromethane. After cooling to −15±5° C. a solution of 17.46 kg (149.86 mol) of chlorosulphonic acid in 20.0 L dichloromethane was metered in and the mixture was stirred for approx. another 30 minutes at −15±5° C. Then the reaction mixture was metered into a solution of 15.0 kg sodium chloride in 85.0 L of water that had been cooled to −7±5° C., and diluted with 15.0 L of dichloromethane. The organic phase was separated off, diluted with 15.0 L of dichloromethane and washed with 30.0 L of sodium hydrogen carbonate solution (5%). After separation of the organic phase once again and dilution with 10 L of dichloromethane, a solution of 11.58 kg (154.20 mol) N-methylaminoethanol in 10.0 L of dichloromethane was slowly metered in at 10±5° C. After the reaction had ended 45.0 L of HCl (3%) and 5.0 L of water were added. The organic phase was separated off, diluted with 10.0 L dichloromethane and the solvent was totally eliminated from the product (C) in vacuo.

Yield: 14.34 kg (71% of theory)

Example 2

Sodium salt of {2-[(4-methoxy-2,6-dimethyl-benzenesulphonyl)-methyl-amino]-ethoxy}-acetic acid (E)

10.00 kg (36.58 mol) of N-(2-hydroxy-ethyl)-4-methoxy-2,6,N-trimethyl-benzenesulphonamide (C) and 6.52 kg (55.97 mol) chloroacetic acid sodium salt (D) were placed in 55.0 L acetonitrile and within approx. 1 hour 27.99 kg (54.87 mol) of potassium tert. butoxide solution was added at 20±5° C. Then the reaction mixture was stirred for approx. 1 hour at 20±5° C. After 52.0 L of solvent had been distilled off, 60.0 L of toluene were added and a further 52.0 L of solvent were distilled off. Then 45.0 L water and 7.56 kg (62.92 mol) hydrochloric acid (30%, industrial grade) were added and the organic phases were separated off at 50° C. After cooling to 30±5° C., 20.0 L acetone and 2.93 kg (36.58 mol) sodium hydroxide solution (50%) were added and inoculated, before the mixture was cooled to 20±5° C. within approx. 1 hour. After 30 minutes stirring at 20±5° C. the suspension was filtered off, the product (E) was washed twice with acetone and dried.

Yield: 10.91 kg (84% of theory)

melting point: 153° C.±3° C.

Example 3

2-{2-[(4-methoxy-2,6-dimethyl-benzenesulphonyl)-methyl-amino]-ethoxy}-N-methyl-N-[3-(4-methyl-piperazin-1-yl)-cyclohexyl]-acetamide L-(+)-tartrate (G)

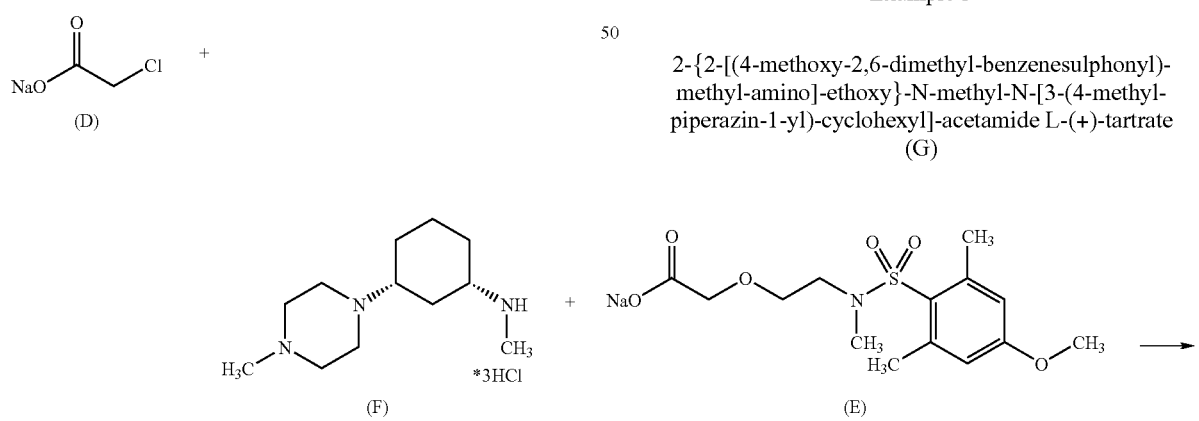

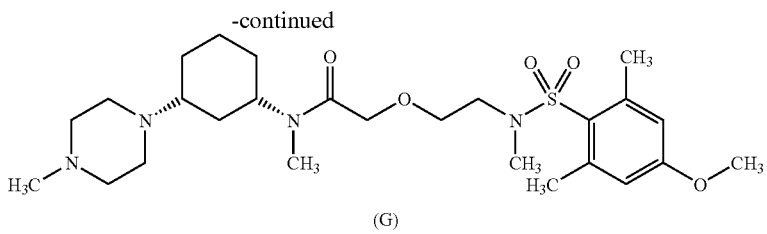

(G)

3.50 kg (10.91 mol) of methyl-[(1S,3R)-3-(4-methyl-piperazin-1-yl)cyclohexyl]-amine tri-hydrochloride (F) and 4.24 kg (12.00 mol) of the sodium salt of {2-[(4-methoxy-2,6-dimethyl-benzenesulphonyl)-methyl-amino]-ethoxy}-acetic acid (E) were suspended in 17.5 L of THF and heated to 50±5° C. Then 21.43 kg (38.19 mol) potassium tert. butoxide solution in tetrahydrofuran, 5.0 L of tetrahydrofuran, 13.89 kg (83.97 mol) of 50% propanephosphonic anhydride in ethyl acetate and a further 5.0 L of tetrahydrofuran were metered in successively and the reaction mixture was stirred for approx. 1 hour at 50±5° C. After the reaction had ended 17.5 L toluene and 19.5 L water were added and the pH of the aqueous phase was adjusted to less than 2.5 with hydrochloric acid (30%). The aqueous phase was separated off, diluted with 2.0 L water and combined at 50° C. with 42 L of methylisobutylketone and a mixture of 4.45 kg (55.65 mol) sodium hydroxide solution (50%, industrial grade) and 3.5 L of water. After approx. 5 minutes' stirring at 50° C. the aqueous phase was separated off and 28.0 L solvent were distilled off in vacuo. The cloudy residue was filtered at 60° C. and the filtrate was combined with 14.0 L of methylisobutylketone. Then the solvent was eliminated completely in vacuo and product (G) was isolated.

Yield: 4.69 kg (82% of theory)
$R_f$=0.45 (CH$_2$Cl$_2$/EtOH/NH$_{3aq.}$=8/2/0.2)

Example 4

Tert-butyl[3-(4-methyl-piperazin-1-yl)-cyclohexyl]-carbamate (J)

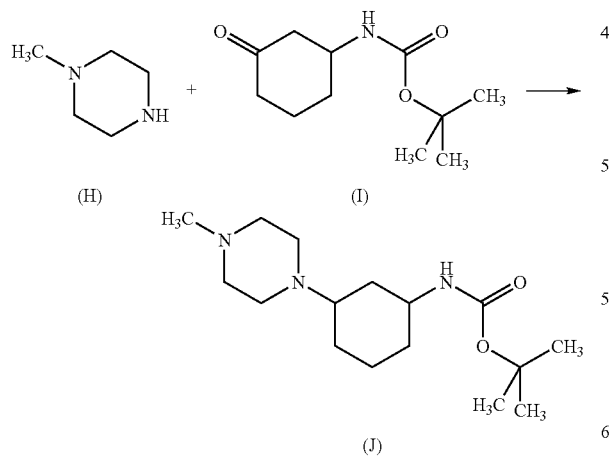

2.6 ml (23.4 mmol) of 1-methylpiperazine (H), 1.0 g (4.69 mmol) of 3-amino-N-tert-butyloxycarbonyl-cyclohexanone (I) (AB Chem) and 2.7 ml (49 mmol) of glacial acetic acid were dissolved in 10 ml of methanol and stirred for 30 minutes at ambient temperature.

Then 1.99 g (9.38 mmol) of sodium triacetoxyborohydride was added batchwise and the mixture was stirred for 2 hours at ambient temperature. Then the reaction solution was combined with hydrogen carbonate solution and extracted with dichloromethane. The solvent was eliminated from the organic phase in vacuo and the residue was subjected to reverse phase chromatography (Varian C18 XRS) (water+5% NH$_3$/acetonitrile=90:10->0:100).

$C_{16}H_{31}N_3O_2$ (297.44)
[M+H]+=298

Example 5

Methyl-[3-(4-methyl-piperazin-1-yl)-cyclohexyl]-amine (K)

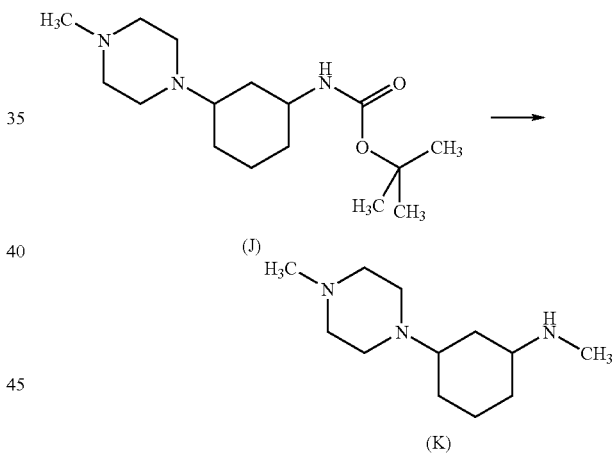

8.57 ml (8.57 mmol) of a 1 M solution of lithium aluminium hydride in toluene were dissolved in 8 ml THF and at ambient temperature slowly combined with 850 mg (2.86 mmol) of product from Example 4 (J) dissolved in 2 ml THF. The reaction solution was stirred for 2 hours at 75° C. Then 1N sodium hydroxide solution and water were added.

The precipitate was suction filtered and the reaction solution was evaporated to dryness.

$C_{12}H_{25}N_3$ (211.35)
[M+H]+=212
HPLC: retention time=0.29 min
Method: Column: Merck Cromolith Speed ROD RP18e, 4.6×50 mm
Detection: 190-400 nm
Eluant A: water/0.1% formic acid
Eluant B: acetonitrile/0.1% formic acid Gradient:

| time in min | % A | % B | flow rate in mL/min |
|---|---|---|---|
| 0.0 | 90.0 | 10.0 | 1.5 |
| 4.5 | 10.0 | 90.0 | 1.5 |
| 5.0 | 10.0 | 90.0 | 1.5 |
| 5.5 | 90.0 | 10.0 | 1.5 |

What is claimed is:

1. Method of preparing compounds of general formula I

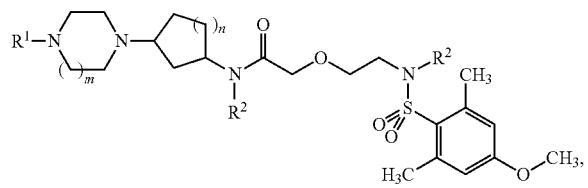
(I)

wherein
m denotes the number 1 or 2,
n denotes the number 0, 1 or 2,
$R^1$ denotes $C_{1-3}$-alkyl or $C_{3-6}$-cycloalkyl and
$R^2$ denotes H or $C_{1-3}$-alkyl,
the enantiomers, the diastereomers, the mixtures and the salts thereof, comprising the steps of:
(a) reacting 3,5-dimethylanisol with chlorosulphonic acid;
(b) reacting 4-methoxy-2,6-dimethylsulphonyl chloride obtained in step (a) with a compound of general formula II

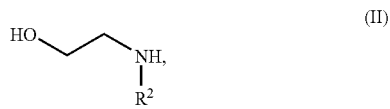
(II)

wherein $R^2$ is defined as mentioned hereinbefore;
(c) reacting a compound of general formula III obtained in step (b)

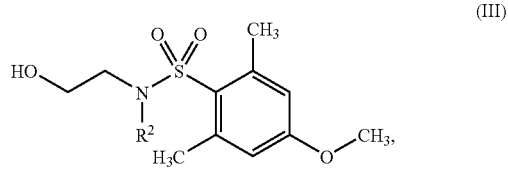
(III)

wherein $R^2$ is defined as mentioned hereinbefore, with a compound of general formula IV

(IV)

wherein X denotes a hydrogen atom, an alkali metal or a $C_{1-4}$-alkyl group, and Y denotes a halogen atom;
(d) coupling a compound of general formula V obtained in step (c)

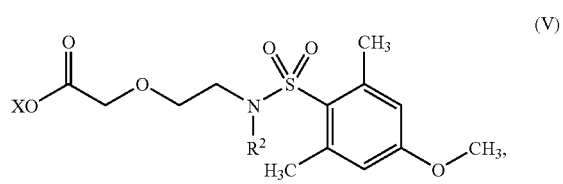
(V)

wherein $R^2$ is defined as mentioned hereinbefore and X denotes a hydrogen atom, an alkali metal, or a $C_{1-4}$-alkyl group, with a compound of general formula VI

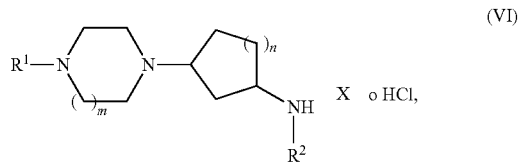
(VI)

wherein m, n, $R^1$ and $R^2$ are defined as mentioned hereinbefore and o denotes one of the numbers 0, 1, 2 or 3; and
(e) isolating a compound of general formula I obtained in step (d).

2. Method of preparing compounds of general formula I according to claim 1, characterised in that
m denotes the number 1,
n denotes the number 1,
$R^1$ denotes $C_{1-3}$-alkyl and
$R^2$ denotes H or $C_{1-3}$-alkyl,
the enantiomers, the diastereomers, the mixtures and the salts thereof.

* * * * *